United States Patent [19]

Auchapt et al.

[11] Patent Number: 4,526,035

[45] Date of Patent: Jul. 2, 1985

[54] DEVICE FOR MEASURING A PRESSURE DIFFERENCE WITHIN A PULSED COLUMN

[75] Inventors: Pierre Auchapt, Bagnols-sur Cèze; Daniel Mathieu, Avignon, both of France

[73] Assignee: Commissariat a l'Energie Atomique, Paris, France

[21] Appl. No.: 384,473

[22] Filed: Jun. 3, 1982

[30] Foreign Application Priority Data

Jun. 3, 1981 [FR] France ................... 81 10985

[51] Int. Cl.³ .............................................. G01F 23/16
[52] U.S. Cl. ........................................ 73/439; 73/302; 210/86
[58] Field of Search ............... 73/302, 439, 299, 303; 210/86

[56] References Cited

U.S. PATENT DOCUMENTS 1,523,110  1/1925  Field ................................ 73/299
4,307,609  12/1981 Rosenblum ...................... 73/439

FOREIGN PATENT DOCUMENTS 2060428  5/1981  Fed. Rep. of Germany .
821072   4/1937  France .
1429352  1/1966  France .
55-47417 4/1980  Japan .
478691   2/1938  United Kingdom .

*Primary Examiner*—S. Clement Swisher
*Attorney, Agent, or Firm*—Kerkam, Stowell, Kondracki & Clarke

[57] ABSTRACT

The invention relates to a device for controlling the pressure within a pulsed column. The device comprises first and second dipping tubes respectively issuing into the column at the level of points $P_1$ and $P_2$, means for introducing a gas into each of the tubes and for bubbling it in the column liquid and means for determining the pressure difference between said tubes. The first and second dipping tubes respectively issue into the column via cavities $C_1$ and $C_2$ having dimensions such that during pressure variations due to pulsation, the gas-liquid interface is always located in each of said cavities and the variations in the gas-liquid interface level in each cavity are inversely proportional to the densities of the liquids present in each cavity. Thus, it is possible to eliminate the prejudicial influence of pressure variations within the liquid due to pulsation. The device can in particular be used for measuring the interface level in the decanter.

11 Claims, 2 Drawing Figures

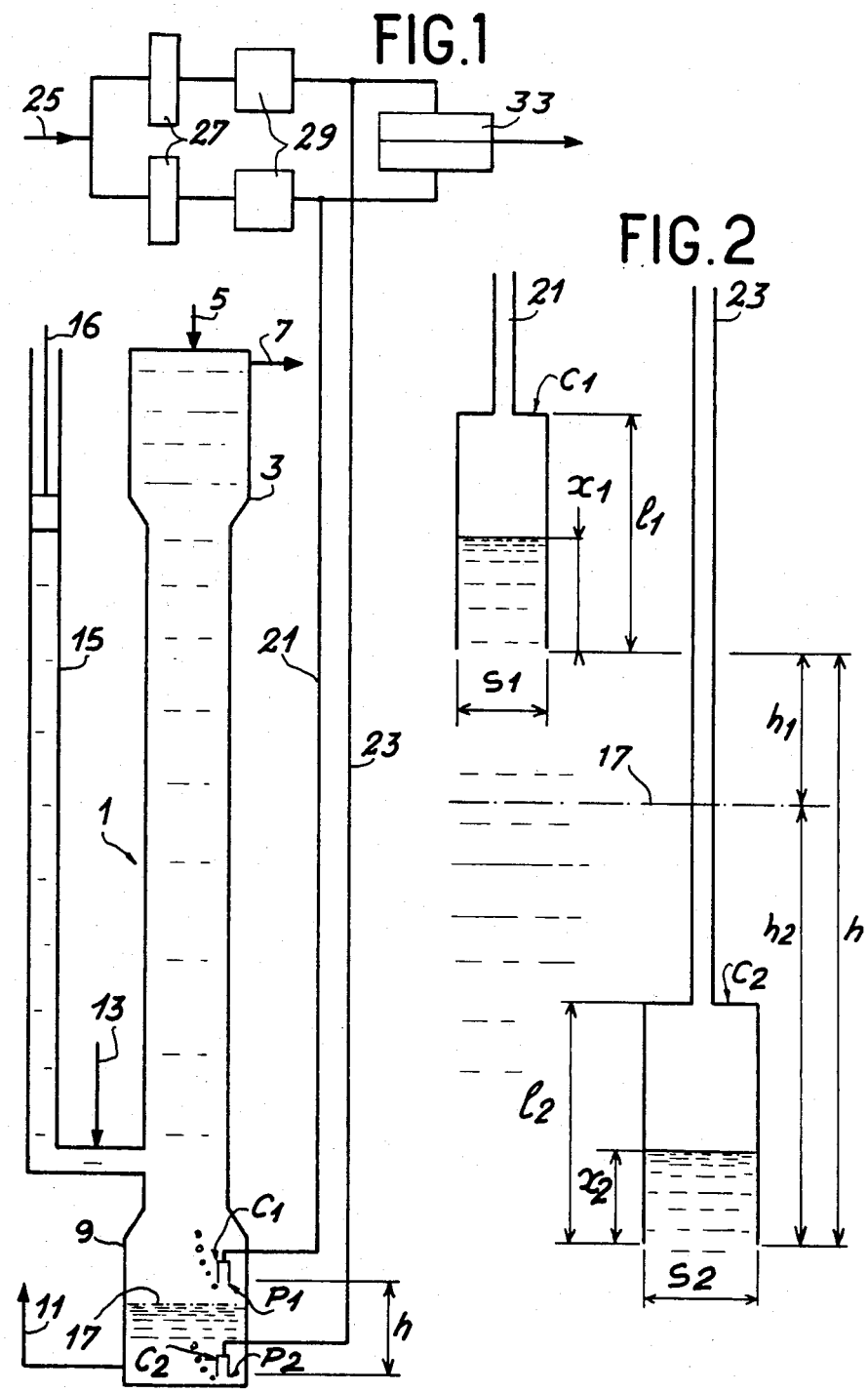

DEVICE FOR MEASURING A PRESSURE DIFFERENCE WITHIN A PULSED COLUMN

BACKGROUND OF THE INVENTION

The invention relates to a device for measuring a pressure difference within a pulsed column, which can in particular be used for determining the density or level of the interface in pulsed columns of irradiated nuclear fuel reprocessing installations.

In irradiated nuclear fuel reprocessing installations, pulsed columns are frequently used in which an aqueous phase is contacted with an organic phase for bringing about the extraction of uranium, plutonium and/or fission products. To ensure a satisfactory operation of such pulsed columns, it is necessary to accurately check the development of certain parameters, in particular the level of the interface in the decanter, the density of the liquid phases circulating in the column and the weight of a liquid column.

Bearing in mind the radioactivity of the phases processed in the column, it is necessary to use for carrying out such checks and inspections very reliable automatic devices, which in particular satisfy the following requirements:

they must not incorporate parts liable to become defective when in contact with radioactive solutions,
they must satisfy nuclear safety conditions,
they must be insensitive to ionizing radiation,
they must be insensitive to high internal pressure variations due to the pulsation,
they must have an excellent corrosion resistance in the presence of the radioactive solutions processed in the column.

It is known that parameters such as the interface level, the weight of a liquid column and the density of a liquid can be determined on the basis of pressure values at one or more points within the column. Conventionally, the pressure is measured in a pulsed liquid by placing a suitable transducer in contact with the liquid and by converting the pressure into a usable electric signal. A faithful measurement, which is e.g. easy to use is obtained if the transducer has an adequate dynamic response. When the solutions circulated in the column are dangerous or corrosive solutions, it is possible to place a buffer liquid between the diaphragm in contact with the liquid and the diaphragm of the transducer. However, such measuring devices cannot be used in the case of the pulsed columns employed for processing radioactive solutions, due to the considerable difficulties encountered in maintaining them and carrying out repairs.

Furthermore, in such columns, the pressure within the liquid is measured by determining the bubble pressure of a gas such as air. Devices usable for this measurement simply comprise dipping tubes, which issue into the liquid of the column at the points where it is desired to measure the pressure, means for producing a compressed gas into these tubes and means for measuring the pressure within the dipping tubes.

In the case of devices of this type, the only part which is in contact with the radioactive liquid is constituted by the dipping tube, which satisfies the requisite conditions. Thus, the dipping tube undergoes little change over a period of time, can easily be unblocked by injecting an appropriate liquid, no constructional problems are encountered in its production for the purpose of satisfying nuclear safety conditions and it is insensitive to ionizing radiation. Moreover, the pressure measuring means can be constituted in this case by a conventional transducer, because the latter is located outside the column in an accessible area and is only in contact with filtered air.

However, such devices are not suitable for measuring pressure in pulsed columns. Thus, in this case, the pressure within the liquid of the column varies significantly with the pulsations, which causes the liquid to rise in the dipping tubes and there is a variation in the level of said liquid as a function of the pulsation. Therefore, the pressure value measured in dipping tubes not correspond to the pressure of the liquid in the column. This problem is more particularly encountered when measuring the interface level in a lower decanter of a pulsed column operating in a continuous organic phase. Thus, for this measurement, it is necessary to be able to detect a low amplitude pressure variation (e.g. approximately 0.3 millibar/1 cm of interface level variation) and this variation is drowned in a background noise of approximately 300 to 600 millibars due to the pulsation, i.e. a background noise which is 1000 to 2000 times higher. Thus, such a device is not suitable for checking the interface level in a pulsed column.

To obviate this disadvantage, consideration has been given to the improvement of such devices by using different systems for reducing the parasitic phenomena due to pulsation. To this end, pneumatic shock absorbers have been used on the dipping tubes. Consideration has also been given to determining the interface level by measuring the pressure difference between two points $P_1$ and $P_2$ of the column by bubbling a gas into so-called "rejected pots", or head pots, as they are sometimes called, which are respectively connected to the liquid level of the column at points $P_1$ and $P_2$. However, these systems are not satisfactory. Thus, when using pneumatic shock absorbers, the measuring chain must be calibrated as a function of the operating parameters of the column, i.e. the pulsating pressure, the pulsating frequency, the flow rate, etc. Therefore, when these parameters vary, it is necessary to recalibrate the measuring chain, which is very difficult to carry out.

In the case of the "rejected pots," or head pots, as they are sometimes called, system it is difficult to carry out on an industrial level due to the hydraulic complexity and the large overall dimensions of the circuits, risks of the pipes connecting the pots to the column becoming dirty and problems caused by a sudden variation in the interface level.

BRIEF SUMMARY OF THE INVENTION

The present invention relates to a device for measuring a pressure difference within a pulsed column, which obviates the disadvantages of the presently known devices.

Therefore, the invention specifically relates to a device for measuring the pressure difference between two points $P_1$ and $P_2$ within a pulsed column comprising first and second dipping tubes issuing respectively into the column at the levels of points $P_1$ and $P_2$, means for introducing into each of said dipping tubes a gas and for bubbling it into the liquid medium of the column, and means for determining the pressure difference between said dipping tubes, wherein the first and second dipping tubes issue respectively into the column via cavities $C_1$ and $C_2$, which are open at their lower end, said cavities $C_1$ and $C_2$ having dimensions such that when pressure variations occur due to the pulsation, the gas-liquid interface is always located in each of the said cavities and the variation $\Delta x_1$ of the gas-liquid interface level in cavity $C_1$ and the variation $\Delta x_2$ of the level of the gas-liquid interface in cavity $C_2$ are such that $\Delta x_1/\Delta x_2$ remains substantially equal to $\rho_2/\rho_1$, $\rho_2$ and $\rho_1$ representing respectively the density of the liquid volume present in the column level with point $P_1$ and the density of the liquid medium in the column level with point $P_2$.

Thus, the presence of these cavities makes it possible to minimise the unfavourable influence of the aforementioned parasitic phenomena. Thus, through using a cavity within which the liquid level varies very little in spite of the pulsations means that a negligible influence are exerted by the height of the liquid in the cavity, together with the inertia and friction.

Advantageously, the cavities are shaped like a vertically positioned straight cylinder and the cross-section of this cylinder is chosen as a function of the extreme operating parameters of the column, particularly the highest planned pulsation pressure and frequency.

For example, it is possible to use cavities having a circular-cross-section with a diameter varying from 20 mm for small columns (cross-section 50 to 80 cm$^2$) to 80 mm for large columns (cross-section exceeding 700 cm$^2$). In general, cavities having a circular-cross-section with a diameter of least 30 mm are used.

It can be assumed that the influence of the variable pressure within the liquid on the pressure measurement is in practice inversely proportional to the cross-section of the cavity. Thus, it is advantageous to use a cavity with the maximum cross-section.

Moreover, to ensure that the gas-liquid interface is always located in the cavity, the latter must have a volume which is at least equal to the minimum volume making it possible to confine the interface within the cavity. Advantageously, the cavity has a volume which slightly exceeds the minimum volume.

In the device according to the invention, the unfavourable influences of the liquid columns present in the cavities $C_1$ and $C_2$ is compensated by using cavities having dimensions such that during pressure variations in the column as a result of the pulsation, the effect of the liquid column in cavity $C_1$ is cancelled out by the effect of the liquid column in cavity $C_2$.

Thus, by measuring the pressure difference between the dipping tubes, a measurement is obtained which is substantially equal to that of the pressure difference between points $P_1$ and $P_2$.

Preferably, cavities $C_1$ and $C_2$ are shaped like vertically positioned straight cylinders and they respectively have cross-sections $S_1$ and $S_2$ such that $S_1/\rho_1$ is equal to $S_2/\rho_2$.

As hereinbefore, cross-section $S_1$ or $S_2$ is chosen as a function of the extreme operating parameters of the column. In the same way, cavities $C_1$ and $C_2$ having a volume which is slightly larger than the minimum volume making it possible to ensure the confinement of the gas-liquid interfaces within said cavities are used. Advantageously, cavities $C_1$ and $C_2$ have a circular-cross-section. The volume $V_1$ of cavity $C_1$ is equal to the volume $V_2$ of cavity $C_2$.

In the same way, the volume of the gas circuit upstream of cavity $C_1$ is substantially equal to the volume of the gas circuit upstream of cavity $C_2$. In particular, this makes it possible to minimise the other parasitic perturbations liable to affect the measurement of the pressure difference.

The device according to the invention is particularly suitable for measuring the level of the interface in the decanter of a pulsed column. In this case, points $P_2$ and $P_1$ are located in the column decanter on either side of the interface and the device also comprises means for determining the level of the interface in the decanter on the basis of the pressure difference between the two dipping tubes, the distance h between points $P_1$ and $P_2$ and the densities $\rho_1$ and $\rho_2$ of the two liquid phases circulating in the column.

The device according to the invention can also be used for measuring the density of a liquid pressure present in a pulsed column. In this case, the points $P_1$ and $P_2$ at which issue the dipping tubes are both located above or below the level of the interface in the decanter and the device comprises means for determining the density of the liquid medium present in the column between points $P_1$ and $P_2$ on the basis of the pressure differences between the two dipping tubes and the distance h between points $P_1$ and $P_2$.

In this case, it is possible to use cavities $C_1$ and $C_2$ having the shape of straight cylinders and having the same cross-section and height.

BRIEF DESCRIPTION OF THE DRAWINGS

The invention is described in greater detail hereinafter relative to non-limitative embodiments and with reference to the attached drawings, wherein show:

FIG. 1 a vertical section through a pulsed column incorporating an interface level measuring device according to the invention.

FIG. 2 a larger-scale view of cavities $C_1$ and $C_2$ of FIG. 1.

DETAILED DESCRIPTION OF THE PREFERRED EMBODIMENTS

In FIG. 1, it is possible to see that column 1 having a circular cross-section has an upper widened portion 3 provided with a heavy phase intake 5 and a light phase outlet 7, together with a lower portion 9 having a widened section provided with a heavy phase outlet 11. In the present case, the lower part 9 acts as a decanter, i.e. the column operates in a continuous light phase. The light phase is introduced into column 1 by pipe 13, which issues into the pulsating tube 15 for transmitting pulses to the two liquid phases contacted in column 1. Tube 15 is provided at its upper end with an air pulsation device 16, whose pressure varies as a function of the time for varying the liquid level in the pulsating tube between two extreme positions and at a given frequency.

In a column of this type, it is general to check the drawing off flow rate of the heavy phase by measuring the level of interface 17 in lower decanter 9. To this end, a device for measuring the pressure difference between two points $P_1$ and $P_2$ located in the decanter and on either side of interface 17 is used. This device comprises a first dipping tube 21, which issues into the decanter level to point $P_1$ and a second dipping tube 23 issuing into the decanter at the level of point $P_2$. Tubes 21 and 23 are respectively connected on the one hand to a compressed air source 25 by rotameters 27 and flow regulators 29, and on the other hand to a differential pressure transducer 33.

According to the invention, dipping tubes 21 and 23 respectively issue into the column at points $P_1$ and $P_2$ via cavities $C_1$ and $C_2$, which are open at their lower end and have a relatively large cross-section compared with that of tubes 21 and 23.

The presence of cavities $C_1$ and $C_2$ makes it possible to very reliably measure the pressure difference, despite the fluctuations in the pressure due to pulsation. Thus, due to the pulsations transmitted by tube 15, pressure p(t) within the liquid varies as a function of time. Two cases can be envisaged as a function of a method of varying the pressure.

(1) Pressure p varies slowly as a function of time, i.e. dp/dt is equal to or below $Q/kV_0$, Q representing the air flow in the column or dipping tube, k is a constant and $V_0$ represents the volume of the dipping tubes upstream of cavities $C_1$ and $C_2$. In this case, dipping tubes 21 and 23 remove the air in an interrupted manner with a flow rate which obviously varies in time, the latter increasing when the pressure decreases and vice versa. Under these conditions, the pressure transmitted to transducer 33 is very close to the true pressure within the liquid and the differential indication is a true reflection of the weight of the liquid column between the two points $P_1$ and $P_2$.

(2) Pressure p varies rapidly as a function of time, i.e. dp/dt exceeds $Q/kV_0$.

Under these conditions, if the dipping tubes 21, 23 are not associated with cavities $C_1$ and $C_2$ and instead directly issue into column 1, the latter only discharge the air in an incidental manner at the time when the pressure is lowest and for what can be a very short time. The rest of the time, the liquid rises or falls in tubes 21 and 23 and the pressures transmitted to the pressure transducer 23 are therefore considerably influenced by the weight of the liquid columns rising in the dipping tubes 21, 23, the inertia of the liquid with a constant speed variation and the friction of the liquid in the dipping tubes.

In view of the fact that the system is never strictly symmetrical between points $P_1$ and $P_2$ and the compressed air supply device, a very considerable error can be introduced into the pressure difference measurement. Thus, for a pulsation frequency of 1 Hz and a pressure amplitude of 600 millibars, the maximum pressure variation dp/dt for a sine wave in the bottom of the pulsed column is substantially equal to 1885 millibars/second.

If each of the tubes 21, 23 has a length of 20 m and a diameter of 8 mm and if the average gas bubbling flow rate is 10 liters/hour, the limit ratio $Q/kV_0$ is 2.8 millibars/second.

Thus, the pressure variation as a function of time is 673 times higher than the permitted limit for which the pressure variations due to pulsations exert an negligible influence on the measurement of the pressure difference between points $P_1$ and $P_2$.

Thus, according to the invention, the end of the dipping tubes 21, 23 is modified so as to make it possible to ignore the aforementioned parasitic influences and in particular the height of the liquid columns rising in dipping tubes 21, 23, the inertia phenomenon and the friction phenomenon.

Therefore, dipping tubes 21, 23 respectively issue into the column via cavities $C_1$, $C_2$, which have dimensions such that during pressure variations in the liquid due to pulsation, the liquid-gas interface is always located within each of the cavities $C_1$, $C_2$ and the level of said interface varies little within each of the cavities. Preferably, cavities $C_1$ and $C_2$ also have dimensions such that during pressure variations due to pulsation, the variation $\Delta x_1$ of the gas-liquid interface level in cavity $C_1$ and the variation $\Delta x_2$ of the gas-liquid interface level in cavity $C_2$ are such that $\Delta x_1/\Delta x_2$ is substantially equal to $\rho_2/\rho_1$, $\rho_2$ and $\rho_1$ representing respectively the density of the liquid medium present in the column level with point $P_1$ and the density of the liquid medium present in the column level with point $P_2$, i.e. in the case of the present drawing, the density $\rho_1$ of the light phase and the density $\rho_2$ of the heavy phase.

As shown in FIG. 2, cavities $C_1$ and $C_2$ are shaped like vertically positioned straight cylinders and have respectively circular-cross-sections $S_1$ and $S_2$ and heights $l_1$ and $l_2$. Sections $S_1$ and $S_2$ are large compared with the cross-section of dipping tubes 21, 23, which makes it possible to limit to a low value the variations of the gas-liquid interface level in cavities $C_1$ and $C_2$ and consequently ignores influence due to liquid friction and inertia.

Preferably, volumes $V_1$ and $V_2$ of cavities $C_1$ and $C_2$ are slightly larger than the minimum volume making it possible to obtain a confinement of the gas-liquid interfaces within cavities $C_1$ and $C_2$.

In exemplified manner, volumes $V_1$ and $V_2$ of cylindrical cavities $C_1$ and $C_2$ complying with this feature are calculated hereinafter. When the pressure in the column is equal to the minimum pressure, the volume occupied by the gas in the gas circuit associated with cavity $C_1$ is equal to $V_0+V_1$, $V_0$ representing the volume of the air pipes upstream of cavity $C_1$ and $V_1$ the volume of the latter.

When the pressure in the column is equal to the maximum pressure, the volume occupied by the gas in the same circuit is equal to $V_0+V_1-\Delta V$ with $\Delta V$ representing the volume occupied by the liquid, which has risen within cavity $C_1$.

If $x_1$ represents the maximum liquid height in $C_1$, we obtain $\Delta V = x_1 S_1$ and the volume occupied by the gas is equal to $V_0+(l_1-x_1)S_1$.

On ignoring the gas quantity introduced into the column between the times when the pressure passes from minimum to maximum, the following relation is obtained for the gas circuit associated with cavity $C_1$:

$$p \text{ min.} [V_0 + l_1 S_1] = p \text{ max.} [V_0 + (l_1 - x_1)S_1]$$

In addition, the minimum volume of cavity $C_1$ making it possible to bring about a confinement of the gas-liquid interface within the said cavity corresponds to $l_1 = x_1$, i.e.:

$$S_1 x_1 = V_0 \frac{p \text{ max.} - p \text{ min}}{p \text{ min.}}$$

and the volume of cavity $C_1$ must be such that:

$$V_1 \geq V_0 \frac{p \text{ max.} - p \text{ min.}}{p \text{ min.}}$$

With regards to cavity $C_2$, it is possible to use a cavity of volume $V_2$ equal to volume $V_1$ of cavity $C_1$. Thus, at point $P_2$, the minimum and maximum pressure values are substantially equal to those at point $P_1$, because the liquid height between points $P_1$ and $P_1$ is low compared with absolute pressure.

In this case, for cavities $C_1$ and $C_2$ to be such that the respective variations $\Delta x_1$ and $\Delta x_2$ of the gas-liquid interface in cavities $C_1$ and $C_2$ satisfy the relation $\Delta x_2/\Delta x_1 = \rho_1/\rho_2$, it is merely necessary for cavities $C_1$ and $C_2$ to respectively have sections $S_1$ and $S_2$ such that $S_1/S_2 = \rho_1/\rho_2$.

Thus, when the pressure increases within the liquid of the column due to pulsations, the volumes occupied by the liquid in the cavities $C_1$ and $C_2$ are substantially equal and corresponds to $\Delta V$. Therefore, we obtain $\Delta x_1 S_1 = \Delta x_2 S_2$ and $\Delta x_2/\Delta x_1 = S_1/S_2 = \rho_1/\rho_2$.

In the case of cavities $C_1$ and $C_2$ having the aformentioned geometrical characteristics, the pressure difference measured by transducer 33 substantially corresponds to the pressure difference between points $P_1$ and $P_2$.

Thus, the pressure in dippingtube 21 measured by transducer 33 is equal to $p_1 - \rho_1 g a x_1$ with $p_1$ representing the pressure of the liquid at point $P_1$ and the pressure in dipping tube 23 measured by transducer 33 is equal to $p_2 - \rho_2 g \Delta x_2$ with $P_2$ representing the pressure of the liquid at point $P_2$.

In view of the fact that cavities $C_1$ and $C_2$ have a large cross-section in order that the values of $\Delta x_1$ and $\Delta x_2$ are low, so that liquid friction and inertia have a negligible influence, the pressure difference $\Delta p$ measured by transducer 33 is equal to $p_2 - p_1 - g(\rho_2 \Delta x_2 - \rho_1 \Delta x_1)$. In view of the fact that $\Delta x_1/\Delta x_2 = \rho_2/\rho_2$, we obtain $\rho_2 \Delta x_2 - \rho_1 \Delta x_1 - 0$.

Furthermore, despite the variations of the liquid level in cavities $C_1$ and $C_2$, as the inertia and friction have been rendered negligible by the large cross-sections $S_1$ and $S_2$ of said cavities, the pressure difference measured by the transducer is equal to the pressure difference within the liquid between points $P_1$ and $P_2$.

On the basis of the value of this pressure difference, it is possible to calculate the value of the interface level 17 on the basis of the following equations:

$$\Delta p = g(\rho_1 h_1 + \rho_2 h_2) \text{ and } h = h_1 + h_2$$

$h_1$ representing the height of the liquid between the interface at point $P_1$, $h_2$ the height of the liquid between the interface at point $P_2$ and $h$ the distance between points $P_1$ and $P_2$.

To obtain this level, transducer 33 is provided with means for determining $h_1$ or $h_2$ on the basis of $\Delta p$, $h$, $\rho_1$ and $\rho_2$ and for emitting a signal representing the interface level value.

As an example, the following table gives the geometrical characteristics of cavities $C_1$ and $C_2$ adapted to the measurement of the interface level in the lower decanter of a pulsed column in which the maximum pressure level with point $P_1$ is $2.5 \cdot 10^5$ Pa and the minimum pressure is $1.5 \cdot 10^5$ Pa for a pulsating pressure of 1 bar and in which a light liquid phase is circulated having a density $\rho_2$ of 820 kg/m$^3$ and a heavy phase is circulated having a density $\rho_1$ of 1150 kg/m$^3$.

TABLE

| Cavity | Volume | Cross-section | Height |
|---|---|---|---|
| $C_1$ | $V_1 = 1$ l | $S_1 = 50.27$ cm$^2$ | $l_1 = 19.9$ cm |
| $C_2$ | $V_2 = 1$ l | $S_2 = 70.50$ cm$^2$ | $l_2 = 14.2$ cm |

In this example, $S_2$ has been calculated as a function of $S_1$ after choosing a diameter of 80 mm for cross-section $S_1$.

The device comprising these two cavities can be used for measuring the interface level in a pulsed column having a cross-section of 930 cm$^2$ and having 8 m of lining with a distance of 70 cm between points $P_1$ and $P_2$. In this case, it is possible to use an air supply flow rate of 10 dm$^3$/hour with an internal volume $V_0$ of the gas circuits upstream of cavities $C_1$ and $C_2$ of 1 dm$^3$, which represents 20 m of pipe with a diameter of 8 mm. Under these conditions, the pressure difference measuring device has proved particularly reliable and is independent of the pulsation pressure between 0 and 1000 millibars. The residual pulsation influence is merely materialised by an oscillation of the signal supplied by transducer 33 having an amplitude proportional to the pulsation pressure (4% of the scale at maximum pressure).

However, on using the same device without cavities $C_1$ and $C_2$, the signal cannot be recorded because the displacement of the measurement is such that the latter is outside the scale of the recording instrument, thus indicating an incorrect measurement of the interface level.

To further improve the reliability of the device according to the invention, it is preferable for the two gas supply circuits associated with cavities $C_1$ and $C_2$ to be strictly identical upstream of the latter. Therefore, the compressed air supply dipping tubes must have the same internal volume (same length and diameter) and any passage irregularities (bends, welds, etc) must as far as possible be common to both. In the same way, it is important that the bubbling air flow rate is constant over a period of time and identical for the two dipping tubes.

The device describes hereinbefore can also be used for measuring the density of the liquid medium present between two points of the column. In this case, cavities $C_1$ and $C_2$ having the same cross-section are used and on the basis of the pressure difference measured by transducer 33, which corresponds to $\rho$ hg, h being the distance between points $P_1$ and $P_2$, the density $\rho$ of the liquid medium present in the column between the two measuring points is determined.

What is claimed is:

1. A device for measuring the pressure difference between two points $P_1$ and $P_2$ within a pulsed column comprising first and second dipping tubes issuing respectively into the column at the levels of points $P_1$ and $P_2$, means for introducing into each of said dipping tubes a gas and for bubbling it into the liquid medium of the column and means for determining the pressure difference between said dipping tubes, wherein the first and second dipping tubes issue respectively into the column via cavities $C_1$ and $C_2$, which are open at their lower end, said cavities $C_1$ and $C_2$ having dimensions such that when pressure variations occur due to the pulsation, the gas-liquid interface is always located in each of the said cavities and the variation of the gas-liquid interface level in cavity $C_1$ and the variation $\Delta x_2$ of the level of the gas-liquid interface in cavity $C_2$ are such that $\Delta x_1/\Delta x_2$ remains substantially equal to $\rho_2/\rho_1$, $\rho_2$ and $\rho_1$ representing respectively the density of the liquid medium present in the column level with point $P_1$ and the density of the liquid medium in the column level with point $P_2$.

2. A device according to claim 1, wherein the cavities $C_1$ and $C_2$ are shaped like vertically positioned straight cylinders and respectively have cross-sections $S_1$ and $S_2$ such that $S_1/\rho_1 = S_2/\rho_2$.

3. A device according to claim 1 wherein the volume $V_1$ of cavity $C_1$ is substantially equal to the volume $V_2$ of cavity $C_2$.

4. A device according to claim 1, wherein cavities $C_1$ and $C_2$ have a circular cross-section.

5. A device according to claim 1, wherein the volume of the gas circuit upstream of cavity $C_1$ is substantially equal to the volume of the gas circuit upstream of cavity $C_2$.

6. A device for measuring the level of the interface in a decanter of the pulsed column, wherein it incorporates a device according to any one of the claims 1 2, 3, 4, or 5 for measuring the pressure difference between two points $P_1$ and $P_2$ located in the decanter of the column of either side of the interface, and means for determining the interface level in the said decanter on the basis of said pressure difference, the distance h between points $P_1$ and $P_2$ and the density $\rho_1$ and $\rho_2$ of the two liquid phases circulating in the column.

7. A device for measuring the density of the liquid medium present in a pulsed column wherein it comprises a device according to any one of the claims 1 2, 3, 4 or 5, for measuring the pressure difference between two points $P_1$ and $P_2$ located in said column and means for measuring the density of the liquid medium present in the column between points $P_1$ and $P_2$ on the basis of said pressure difference and the distance h between points $P_1$ and $P_2$.

8. A device according to claim 2 wherein the volume $V_1$ of cavity $C_1$ is substantially equal to the volume $V_2$ of Cavity $C_2$.

9. A device for measuring the level in the interface in a decanter of the pulsed column, wherein it incorporates a device according to claim 8 for measuring the pressure difference between two points $P_1$ and $P_2$ located in the decanter of the column on either side of the interface, and means for determining the interface level in the said decanter on the basis of said pressure difference, the distance h between points $P_1$ and $P_2$ and the density $\rho_1$ and $\rho_2$ of the two liquid phases circulating in the column.

10. A device for measuring the density of the liquid medium present in a pulsed column, wherein it comprises a device according to claim 8 for measuring the pressure difference between two points $P_1$ and $P_2$ located in said column and means for measuring the density of the liquid medium present in the column between points $P_1$ and $P_2$ on the basis of said pressure difference and the distance h between points $P_1$ and $P_2$.

11. A device according to claim 10 wherein the cavities $C_1$ and $C_2$ are shaped like straight cylinders with the same cross-section.

* * * * *